US00PP21962P3

(12) United States Plant Patent
Adam, Jr.

(10) Patent No.: US PP21,962 P3
(45) Date of Patent: May 31, 2011

(54) ***TIARELLA* PLANT NAMED 'OCTORARO'**

(50) Latin Name: *Tiarella cordifolia*
Varietal Denomination: Octoraro

(75) Inventor: Sinclair A. Adam, Jr., Coatesville, PA (US)

(73) Assignee: Plants Nouveau—a division of Treadwell Palmer International, Inc., Baltimore, MD (US)

( * ) Notice: Subject to any disclaimer, the term of this patent is extended or adjusted under 35 U.S.C. 154(b) by 0 days.

(21) Appl. No.: 12/589,995

(22) Filed: Nov. 2, 2009

(65) Prior Publication Data

US 2011/0107487 P1 May 5, 2011

(51) Int. Cl.
*A01H 5/00* (2006.01)

(52) U.S. Cl. ..... Plt./486

(58) Field of Classification Search ..... Plt./486
See application file for complete search history.

*Primary Examiner* — June Hwu
(74) *Attorney, Agent, or Firm* — Penny J. Aguirre

(57) ABSTRACT

A new and distinct *Tiarella cordifolia* plant characteristized by its large, lobed foliage with purple markings and white blooms.

2 Drawing Sheets

Botanical classification: *Tiarella cordifolia.*
Varietal denomination: 'Octoraro'.

SUMMARY OF THE INVENTION

The new *Tiarella cordifolia* was selected during 2007 as a seedling from the garden at the Nursery of Sinclair A. Adam Jr. at Coatesville, Pa., U.S.A. The exact parentage of the new variety is unknown. It resulted from seedlings grown from open-pollinated plants of *Tiarella cordifolia*, and *Tiarella cordifolia* var. *collina.* Several hundred plants are grown for seed production, and some or all of these plants are likely included in the parentage of the new variety of the present invention.

The new variety has been carefully preserved and studied since the time of its discovery. Had such new variety not been discovered and preserved, it would have been lost to mankind.

It was found that the new *Tiarella cordifolia,* variety of the present invention exhibits the following combination of characteristics: (a) exhibits a compact mounding clump growth habit with substantial runners, (b) forms attractive white flowers on branched flower stalks, (c) forms lobed ovate green leaves having a matte finish during the summer that bear maroon markings primarily along the leaf veins, and this pigment expands in the summer outward from along the veins. In fall the leaves turn golden yellow with red veins of variable intensity, and (d) is particularly well suited for growing as a distinctive ornamental ground cover, creating a dense stand in a season.

The new variety of the present invention can be readily distinguished from other previously known varieties of the species in view of the distinctive combination of characteristics discussed herein. The red, and green spring & summer foliage and fall color is considered to be particularly noteworthy.

The new variety well meets the needs of the horticultural industry and expands the choices of ornamental ground covers which fills in as a stand well. It performs well wherever a ground cover is desired, and is particularly well suited for use as a border planting, use in shaded areas, and for ecology and restoration casting open pollinated seedlings, and asexual runners.

The runners (stolons) and flower stems of clumps have been used to asexually propagate the new variety at Delhi, N.Y. (laboratory), and Coatesville, (breeder and Nursery) Pa., U.S.A. It has been found that the distinctive combination of characteristics of the new variety is firmly fixed and is reliably transmitted to succeeding generations. During observations to date, the new variety has been found to be readily amenable to such propagation.

The new variety 'Octoraro' can be compared to 'Elizabeth Oliver' (not patented), which differs from 'Octoraro' in having foliage that turns purple rather than golden yellow with red veins in fall. 'Octoraro' can also be compared to cultivars from the same breeding program, 'Delaware' (U.S. patent application Ser. No. 12/589,997), 'Lehigh' (U.S. patent application Ser. No. 12/589.998), and 'Susquehanna' (U.S. patent application Ser. No. 12/589.996). 'Delaware' differs from 'Octoraro' in having foliage that turns red in fall rather than golden yellow with red veins. 'Lehigh' differs from 'Octoraro' in lacking red colored runners, and having foliage that is less pubescent and has more maroon pigment between the veins in summer. 'Susquehanna' differs from 'Octoraro' in having foliage that turns red with green margins in fall rather than golden yellow with red veins.

DETAILED BOTANICAL DESCRIPTION

Figure 1:
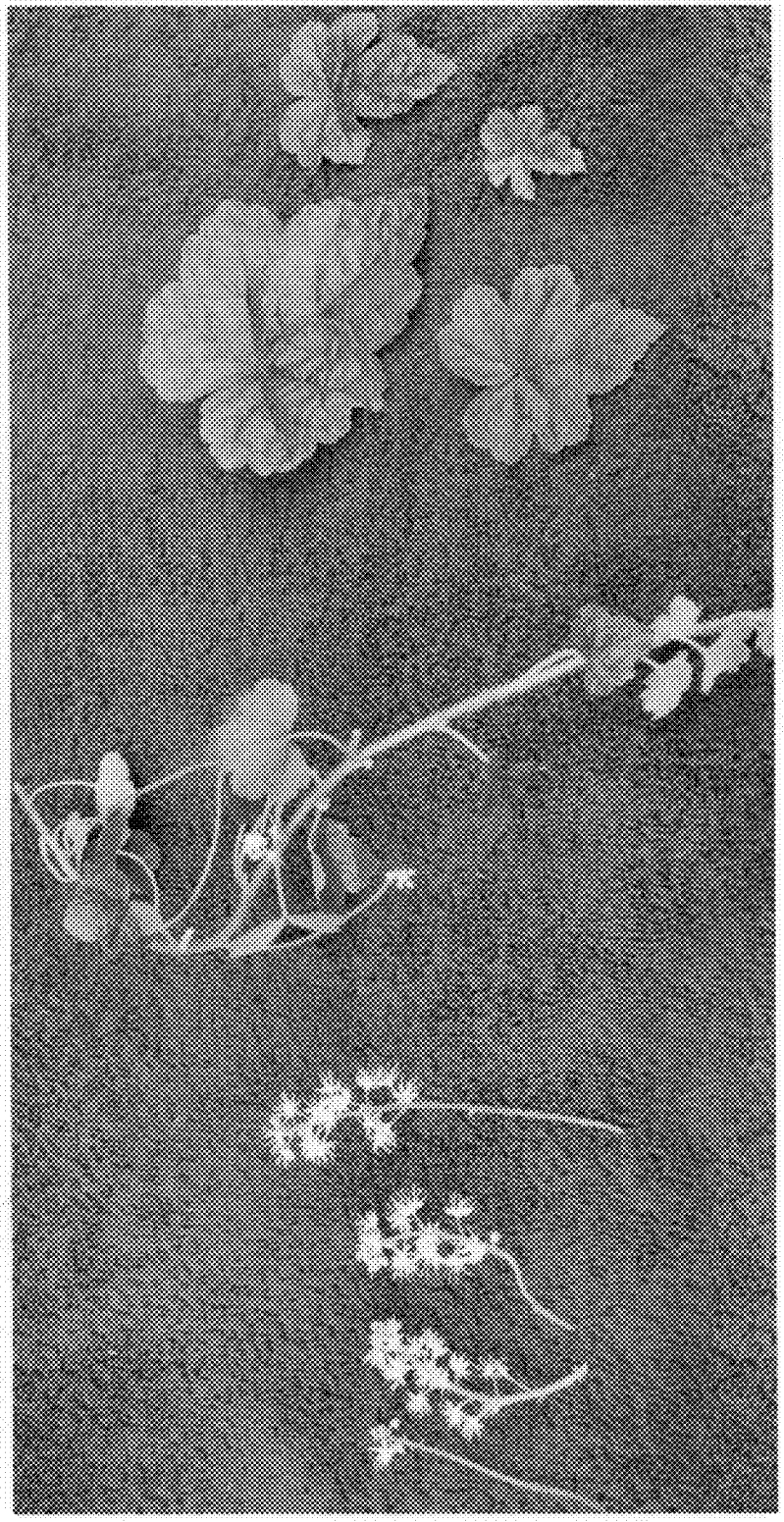
FIG. 1: shows inflorescences on the left (from bud on the left to full bloom on the right), a stolon in the middle, and the upper leaf surface of newly formed leaves in early spring.
Figure 2:
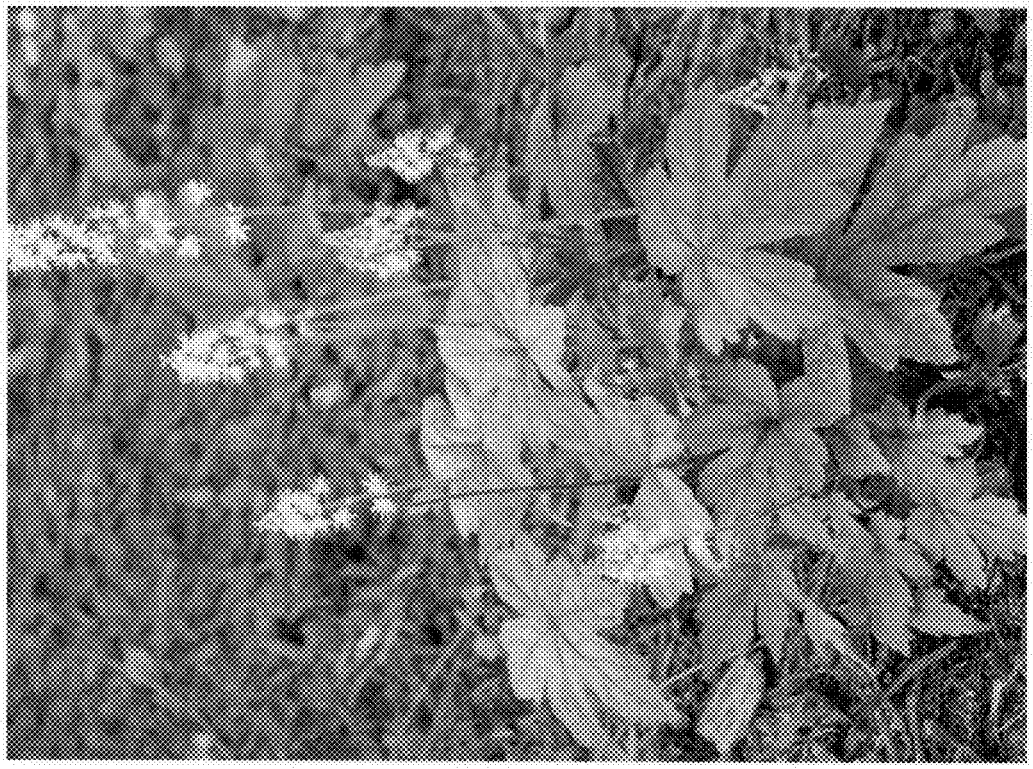
FIG. 2: shows a two year-old plant in the ground in Baltimore, Md. in May and show typical mature foliage characteristics when in bloom.

The following is a detailed description of the new variety that was obtained while observing plants being grown outdoors, and in the greenhouse during 2007-2008 at Coatesville, Pa., U.S.A. The plants were approximately two years of age and were being grown on their own roots. The chart used in the identification of color is The R.H.S. Colour Chart of The Royal Horticultural Society, London, England. More common color terms are to be accorded their ordinary dictionary significance.

Botanical classification: *Tiarella cordifolia* 'Octoraro'.

Plant:

*Habit.*—Compact mounding clump, several runners.

*Type.*—Evergreen.

*Height.*—Approximately 15 to 20 cm without blooms, and approximately 28 to 34 cm with blooms.

*Width.*—Approximately 30-35 cm.

*Stolons.*—177D in color, surface is pubescent with hairs <1 mm in length, internode length an average of 4 cm, stolons leaves are similar to the young leaves in color, however the leaves are more ovate-rounded in shape, have less or lack maroon vein coloration.

Foliage:

*Type.*—Simple.

*Shape.*—Ovate to broadly ovate, palmately five-lobed with an elongated central lobe having two sub-lobes, and irregularly crenate margins on all lobes having mucronate teeth. Each tooth has a small point, which is relatively firm with a leaf vein extending to the end of the tip.

*Length.*—Approximately 10 to 12 cm.

*Width.*—Approximately 9 to 11 cm.

*Margins.*—Incised with dentation, which is more pronounced on more mature leaves.

*Apex.*—The lobes are broadly obtuse to rounded and cuspidate.

*Base.*—Cordate.

*Texture.*—Upper surface; slightly rugose with a velvet glossy finish with hairs about 2 mm in length and 2 mm apart, lower surface; glabrous.

*Arrangement.*—Basal clump, with branched runners 6 to 8 in number, usually 20 to 38 cm in length.

*Venation.*—Palmately reticulate.

Young foliage: On the upper surface Yellow-Green Group 144A to 144B, and Greyed-Purple Group 187A at the center and along the main vein, and on the lower surface Yellow-Green Group 146B to 146C.

Adult foliage: On the upper surface Green Group 137B to 137D, and Brown Group 200B at the center and along the main vein, and on the lower surface Yellow-Green Group 146B to Greyed-Green Group 191A.

Fall foliage: Both the ventral leaf surface (upper) and the dorsal leaf surface (lower) are characterized by areas of light red and darker reddish-purple that are near and through the following colors: Red Group 49D and Red-Purple Group 62D in the lighter areas to Red Group 53D and Greyed-Purple Group 186B in the mid-tones to Greyed-Purple Group 187A and 187B in the darker areas. The dorsal leaf surface exhibits a slightly glossier appearance when compared to the more matte appearance of the ventral leaf surface that commonly is increased in expression in the autumn foliage.

Petiole: The length commonly varies from approximately 9 to 15 cm, and the diameter commonly is approximately 2 to 3 mm, surface is pubescent with hairs 2 mm in length, Greyed-Orange Group 177B in color.

Inflorescence:

*Type.*—Raceme and perfect (bisexual).

*Number.*—Approximately 30 to 50 blooms per raceme.

*Bearing.*—On a branched stalk commonly having a height of approximately 28 to 34 cm, with up to 3 to 4 short side branches. Side branches are 6 to 10 cm in length, bearing 15 to 20 blooms.

*Lastingness of inflorescence.*—About 3 weeks.

*Flower buds.*—Ellipsoid in shape, perigynous, about 3 mm in depth and 25 mm in width, 65C in color.

*Calyx.*—Five-lobed, about 1.1 cm in diameter, and White Group NN155C in color.

*Petals.*—Five.

*Petal shape.*—Triangular.

*Stamens.*—Ten, 3 mm in length. Anthers Coral Red Group 36 D.

*Pistil.*—One, about 4 mm in length.

*Flower size.*—Approximately 9 to 11 mm on average per floret.

*Color.*—On the dorsal surface White Group 155B and on the ventral surface White Group 155A.

*Fragrance.*—Slight and sweet.

*Pedicel.*—Approximately 8 to 9 mm in length on average, Red-Purple Groups 63B in color.

Development:

*Vegetation.*—Clump-forming, with runners (stolons).

*Blooming.*—Abundantly when initially blooms during May/June and sporadically thereafter during the summer and fall.

*Resistance to disease.*—No susceptibility to diseases has been noted during observations to date.

*Hardiness.*—Has proven to grow well in U.S.D.A. Hardiness Zones No. 4 to 7.

*Propensity to form fruit/seeds.*—Approximately 0.2 grams per (1 year old) plant (about 600 seeds).

Plants of the new 'Octoraro' variety have not been observed under all possible environmental conditions to date. Accordingly, it is possible that the phenotype expression may vary somewhat with changes in light intensity and duration, cultural practices, and other environmental conditions.

I claim:

1. A new and distinct *Tiarella* plant as herein illustrated and described.

* * * * *